United States Patent
Engelhardt et al.

(10) Patent No.: US 6,266,148 B1
(45) Date of Patent: Jul. 24, 2001

(54) METHOD FOR MEASURING SURFACES BY CONFOCAL MICROCOPY

(75) Inventors: Johann Engelhardt, Bad Schonborn; Thomas Zapf, Speyer, both of (DE)

(73) Assignee: Leica Microsystems Heidelberg GmbH, Mannheim (DE)

( * ) Notice: Subject to any disclaimer, the term of this patent is extended or adjusted under 35 U.S.C. 154(b) by 0 days.

(21) Appl. No.: 09/147,976

(22) PCT Filed: Sep. 30, 1997

(86) PCT No.: PCT/DE97/02239

§ 371 Date: May 17, 1999

§ 102(e) Date: May 17, 1999

(87) PCT Pub. No.: WO98/14753

PCT Pub. Date: Apr. 9, 1998

(30) Foreign Application Priority Data

Oct. 1, 1996 (DE) .............................................. 196 40 496

(51) Int. Cl.[7] .................................................. G01B 11/24
(52) U.S. Cl. .............................................................. 356/609
(58) Field of Search ..................................... 356/376, 609

(56) References Cited

U.S. PATENT DOCUMENTS

| | | |
|---|---|---|
| 4,732,473 | 3/1988 | Bille et al. . |
| 5,120,953 * | 6/1992 | Harris .................................. 250/227.2 |
| 5,448,359 * | 9/1995 | Schick et al. .......................... 356/376 |
| 5,532,873 | 7/1996 | Dixon . |
| 5,690,490 * | 11/1997 | Cannon et al. ........................ 433/226 |
| 5,912,768 * | 6/1999 | Sissom et al. ........................ 359/629 |

FOREIGN PATENT DOCUMENTS

PCT/AU89/ 00298 7/1989 (WO) .

* cited by examiner

Primary Examiner—Richard A. Rosenberger
(74) Attorney, Agent, or Firm—Simpson, Simpson & Snyder, L.L.P.

(57) ABSTRACT

The invention relates to a method for measuring surfaces by confocal microscopy using the reflection method, specially to measure the superficial profiles (1) of treated or drilled teeth (2). The invention seeks to eliminate mistakes occurring when very inclined areas are measured. To this end, the method disclosed is characterized by a confocal representation with enhanced dynamics (relative sensitivity) enabling it to project both the retro-reflections and the weak scattered light (3) or fluorescent light of each focal plane (8).

4 Claims, 2 Drawing Sheets

METHOD FOR MEASURING SURFACES BY CONFOCAL MICROCOPY

BACKGROUND OF THE INVENTION

The invention concerns a process for surface measurement using confocal microscopy in a reflection process, especially for measuring the surface profile of teeth in the untreated and in the treated or drilled conditions.

This is essentially a process for measurement of surfaces of any type and any contour. Various processes for surface measurement are already known in practice.

For instance, a line of light can be projected on the object with a light sectioning sensor, and observed at an angle with a CCD camera. The geometric deformation of the line is measured. The height differences on the object are computed from this deformation. By moving the object under the sensor—perpendicularly to the light line—and by repeated measurement, a surface form can be measured or determined from a series of profiles.

The light-sectioning sensor is indeed a simply designed and thus a robust sensor, but the oblique lighting which it requires causes unilateral shading of steep surfaces. That causes asymmetries in the imaging, or inaccuracies. Furthermore, error can be introduced into the measurements because of scattering of light from various depths of, for instance, an at least partially transparent tooth material.

Furthermore, it is already known in practice that surfaces can be scanned with confocal microscopy so as to generate three-dimensional pictures of the surface. In this respect, it is only necessary to refer to an article by J. Engelhardt and W. Knebel in Physik in unserer Zeit' [Physics in Our Time], Vol. 24, 1993, No. 3, titled "Confokale Laserscanning-Mikroskopie" [Confocal Laser Scanning Microscopy], and one by D. K Hamilton and T. Wilson in Appl. Phys., B27, 211–213, 1982, titled "Three-dimensional Surface Measurement Using the Confocal Scanning Microscope". Confocal microscopy is very specially suited to surface measurements of tooth surfaces, because this process images only those structures which are exactly in the focal plane of the microscope objective. Thus measurement errors due to the partially transparent tooth material are effectively avoided. To be sure, the method of reflection measurement with the usual confocal microscope fails at steep transitions or flanks if their angle is greater than the aperture angle of the objective, because then the reflection no longer enters the objective, and is lost for evaluation. (See P. C. Cheng and R. G. Summers in: "Handbook of Biological Confocal Microscopy", Plenum Press, New York, 1989, Chapter 17.)

SUMMARY OF THE INVENTION

Therefore this invention is based on the objective of providing a process for surface measurement with which it is possible to measure surfaces of partially trasparent materials, and surface profiles with steep flanks, without problems. This process should be very particularly suitable for use in dentistry, that is, to measure the surface profile of teeth in the untreated and in the treated or drilled conditions.

The surface measurement process according to the invention attains the objective stated above by a process for surface measurement using confocal microscopy in a reflection mode, especially to measure the surface profile of treated or drilled teeth, which is characterized by confocal imaging with high dynamic range (relative sensitivity) so as to image reflections and also weak scattered light or fluorescent light from the particular focal plane.

It is learned here for the first time, according to the invention, that confocal microscopy is quite particularly suited to surface measurement of partially transparent materials, because in confocal microscopy only those structures which are exactly in the particular focal plane of the microscope objective are imaged. It is also learned that the disadvantage of ordinary reflection confocal microscopy with respect to the aperture problem mentioned above can be eliminated by utilizing scattered light or fluorescent light from the particular focal plane for the usual evaluation of the reflection.

The evaluation of the scattered or fluorescent light can be accomplished in a further manner according to the invention through confocal imaging with a high dynamic range, i.e., with high relative sensitivity, so that it is possible to image both strongly reflecting flat surfaces and also to show the scattered or fluorescent light even on steep flanks. Accordingly, imaging is possible by the process according to the invention even if the light reflected from steep flanks misses the objective so that, in the usual reflection process, no profilometry can be done. Finally, the scattered light is always used for evaluation if imaging is no longer possible in the absence of specular reflections by the usual confocal microscopy.

As already mentioned above, the detector signal is digitized at high resolution, particularly advantageously with a dynamic range substantially greater than 8 bits. The relative sensitivity, or dynamic range, of the confocal imaging can be 16 bits for very particularly effective utilization of the weak scattered light or fluorescent light in the vicinity of steep surface slopes.

An algorithm is provided to evaluate elevations, or to produce the surface profile, using weak scattered light. It takes into consideration, or tolerates, the high dynamic range of the system. This algorithm takes the nearest, or indirectly adjacent focal planes into consideration by interpolating, with the higher intensities in the local region being relatively over-weighted so as to reduce the dependence on the background signals. Finally, a suitable algorithm is provided, so that, after detection of the scattered light signal and after high-resolution digitizing, an adequate height evaluation can be made from the digitized signal.

It must be emphasized here that the surfaces can also be scanned with a dark-field system. Either a point light source or a light source appropriately diaphramged can be provided.

In the area of application to dentistry, and particularly to producing exactly fitted inlays instead of the usual amalgam fillings, it is very specially advantageous first to scan the surface of the untreated tooth and to store the detected values, preferably digitized and already processed to give the height profile. In the next step the tooth is treated or drilled. Then the treated or drilled tooth is scanned again, again with storage of the values giving the surface profile of the treated tooth. From the difference between the two surface profiles, or from the values across the surface profile, the surface, or the exact measurements, are calculated for the inlay required so as to give optimal occlusion of the treated tooth.

It is highly advantageous, to get particularly high precision in processing the inlay, if the inlay being produced is scanned after an initial processing, and if the further processing is done by means of correction values obtained by a comparison of the actual and desired values. Correction to verify the inlay shape is possible to the extent that, with repetition of this process, high precision is possible in producing the inlay and optimal occlusion is possible. The measures described above also allow consideration of inaccuracies caused by the equipment or the tools, such as tool wear, to be taken into consideration so that optimal fitting of the inlay and thus optimal occlusion are possible even with a tolerance range at the processing station.

It is also possible that, in a subsequent step, the cavity produced in the tooth may be filled with a plastic composition so that, when the patient bites on it, the contact points with the opposing teeth are marked in the plastic mass. Then the surface profile generated in that way is scanned, the measurements obtained with respect to the surface profile are stored, and they are taken into consideration in calculating the surface or dimensions of the inlay to be produced.

BRIEF DESCRIPTION OF THE DRAWINGS

Now there are various possibilities for designing and developing the teaching of this invention in an advantageous manner. Reference is made to the following explanation of one example embodiment of the invention by means of the drawing. The generally preferred designs and developments from the teaching are explained in connection with the explanation of the preferred example embodiment of the invention. The drawing shows.

DETAILED DESCRIPTION OF THE PREFERRED EMBODIMENTS

The figures show schematically the principle of an example embodiment of the process according to the invention for surface measurement using confocal microscopy, with the specific case of measurement of the surface profile 1 of a tooth 2 indicated schematically.

The invention provides confocal imaging with a high dynamic range, i.e., with high relative sensitivity, for imaging both reflections and weak scattered light 3 from the particular focal plane. The detected signal is digitized with high resolution with a dynamic range greater than 8 bits.

Figure 1:
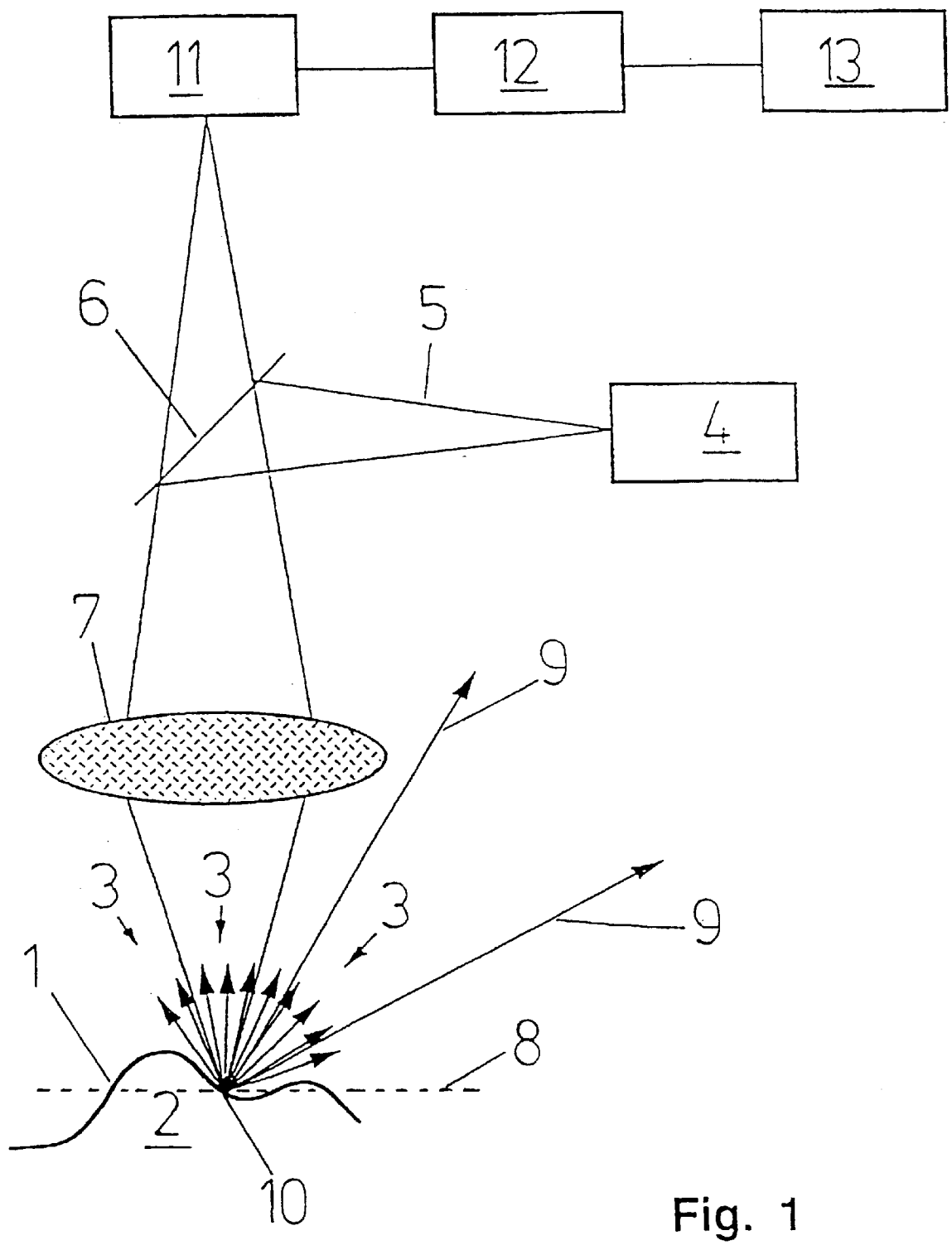
FIG. 1 an application of the process according to the invention in a schematic representation of one example embodiment, and FIG. 2 a schematic representation of another example embodiment of the process according to the invention with a dark-field system.

According to the depiction in FIG. 1, light emitted from a light source 4, or the light beam 5, impinges on a beam splitter 6, and from there it is directed through an objective lens 7 onto the surface or surface profile 1 of the tooth 2. In the depiction selected here, the focal plane 8 lies on a flank which is so steep that the specularly reflected beam 9 no longer strikes the objective lens 7. That is because the angle of the flank in this case is greater than the aperture angle of the objective lens 7.

FIG. 1 also shows that the non-specular diffuse scattered light 3 from the focal point 10 passes to or through the objective lens 7 and through the beam splitter to the detector 11. For simplicity, any parts such as pinholes or diaphragms or the like in the light path are omitted from the depiction. In any case, measurements from the detector 11 are digitized at high resolution and then submitted to a height evaluation to obtain the surface profile 1. The digitizing and height evaluation can be done by an electronic control system 12 or by a computer 13.

Figure 2:
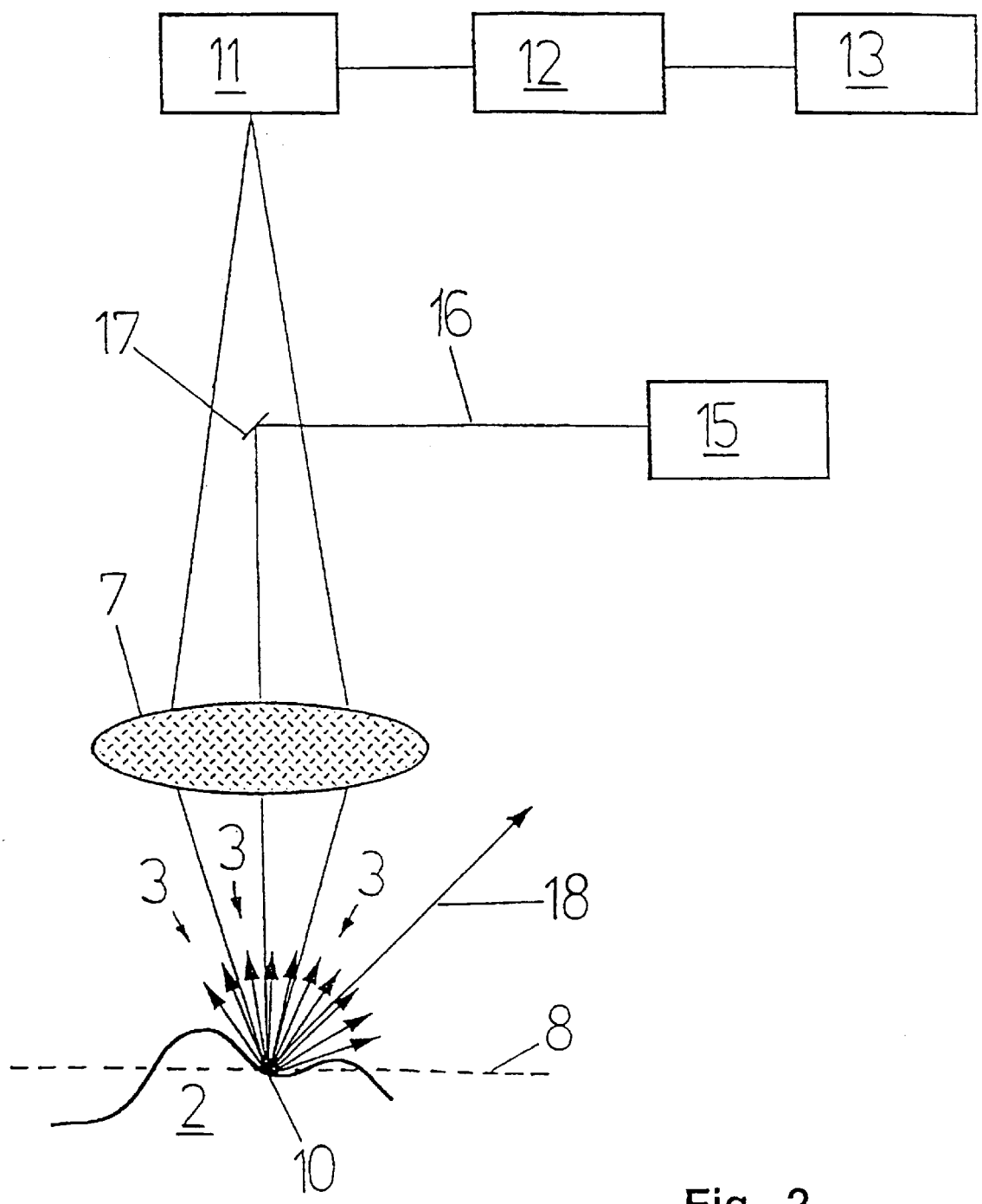

The example embodiment shown in FIG. 2 differs from that of FIG. 1 by showing an application of confocal microscopy in a dark-field system. The light beam 16 from a point source of light 15 goes from a reflector 17 through the objective lens 7 to the surface of the tooth 2. The light beam strikes a surface which is slanted so that the specularly reflected beam 18 does not return to the objective lens 7. Otherwise, to avoid repetitions, see the description for FIG. 1.

Finally, it should be noted that utilization of weak scattered light or fluorescent light is necessary for confocal imaging by the process according to the invention. That makes possible high sensitivity, or a high dynamic range, for evaluating the scattered light and for profilometry, at least including the scattered light at steep flanks.

List of Reference Symbols

1. Surface profile
2. Tooth
3. Scattered light
4. Light source (FIG. 1)
5. Light beam (FIG. 1)
6. Beam splitter
7. Objective lens
8. Focal plane
9. Specularly reflected light (FIG. 1)
10. Focal point
11. Detector
12. Electronic control system
13. Computer
15. Point source of light (FIG. 2)
16. Light beam (FIG. 2)
17. Reflector
18. Reflected beam (FIG. 2)

What is claimed is:

1. A method of measuring a surface of a tooth using confocal microscopy in a reflection process for purposes of a dental inlay, said method comprising the steps of:

(A) scanning said surface prior to treatment of said tooth to detect a series of images of both reflections and weak scattered light or fluorescent light from said surface in a particular focal plane by confocal imaging with high dynamic range to generate a signal;

(B) generating a three-dimnensional digitized representation of said surface of said untreated tooth from said signal using an algorithm which takes said high dynamic range into consideration, and storing said three-dimnensional digitized representation of said surface of said untreated tooth;

(C) repeating steps (A) and (B) with respect to a surface of said tooth after a hole has been drilled in said tooth to store a three-dimensional digitized representation of said surface of said drilled tooth; and (D) calculating a three-dimensional digitized representation of a desired surface of said inlay from the difference in said three-dimensional digitized representations of said surface of said treated tooth and said surface of said drilled tooth.

2. The method according to claim 1, further comprising the steps of filling said drilled hole with a deformable compound so that contact points with opposing teeth are marked by biting on said compound, repeating steps (A) and (B) with respect to a surface of said tooth and marked compound to store a three-dimensional digitized representation of said surface of said tooth and marked compound, and using said three dimensional digitized representation of said surface of said tooth and marked compound in calculating said three-dimensional digitized representation of said desired surface of said inlay.

3. The method according to claim 2, further comprising the steps of forming said inlay based on said three-dimensional digitized representation of said desired surface of said inlay, repeating steps (A) and (B) with respect to a surface of said actually formed inlay to store a three-dimensional digitized representation of said surface of said actually formed inlay, comparing said three-dimensional digitized representation of said surface of said actually formed inlay with said three-dimensional digitized representation of said desired surface of said inlay, and further forming said inlay to reduce differences between surface of said actually formed inlay and said desired surface of said inlay.

4. The method according to claim 1, further comprising the steps of forming said inlay based on said three-dimensional digitized representation of said desired surface of said inlay, repeating steps (A) and (B) with respect to a surface of said actually formed inlay to store a three-dimensional digitized representation of said surface of said actually formed inlay, comparing said three-dimensional digitized representation of said surface of said actually formed inlay with said three-dimensional digitized representation of said desired surface of said inlay, and further forming said inlay to reduce differences between surface of said actually formed inlay and said desired surface of said inlay.

* * * * *